US012582871B2

(12) United States Patent
Agrawal et al.

(10) Patent No.: US 12,582,871 B2
(45) Date of Patent: Mar. 24, 2026

(54) ACTIVITY TRACKING FOR MULTIPLE USERS ON A DEVICE

(71) Applicant: Motorola Mobility LLC, Chicago, IL (US)

(72) Inventors: Amit Kumar Agrawal, Bangalore (IN); Krishnan Raghavan, Bangalore (IN)

(73) Assignee: Motorola Mobility LLC, Chicago, IL (US)

( * ) Notice: Subject to any disclaimer, the term of this patent is extended or adjusted under 35 U.S.C. 154(b) by 56 days.

(21) Appl. No.: 18/410,139

(22) Filed: Jan. 11, 2024

(65) Prior Publication Data

US 2025/0229130 A1     Jul. 17, 2025

(51) Int. Cl.
| | |
|---|---|
| *A63B 24/00* | (2006.01) |
| *A61B 5/11* | (2006.01) |
| *G06V 40/12* | (2022.01) |
| *G06V 40/16* | (2022.01) |
| *G10L 17/00* | (2013.01) |

(52) U.S. Cl.
CPC ........ *A63B 24/0062* (2013.01); *A61B 5/1118* (2013.01); *G06V 40/1365* (2022.01); *G06V 40/172* (2022.01); *G10L 17/00* (2013.01)

(58) Field of Classification Search
CPC .............. A63B 24/0062; A61B 5/1118; G06V 40/1365; G06V 40/172; G10L 17/00
See application file for complete search history.

(56) References Cited

U.S. PATENT DOCUMENTS

| | | | | |
|---|---|---|---|---|
| 9,467,795 B2 * | 10/2016 | Kreitzer | .................. | H04W 4/50 |
| 9,483,957 B1 * | 11/2016 | Fuemmeler | ............ | G09B 5/125 |
| 2015/0181314 A1 * | 6/2015 | Swanson | ................ | G01C 21/20 |
| | | | | 340/870.07 |
| 2016/0069679 A1 * | 3/2016 | Jackson | .................... | G01C 5/00 |
| | | | | 702/160 |
| 2016/0256082 A1 * | 9/2016 | Ely | ...................... | A61B 5/7282 |
| 2018/0056127 A1 * | 3/2018 | Den Hollander | .... | A63B 21/063 |
| 2020/0306588 A1 * | 10/2020 | Woelfle | ................. | G06F 3/0482 |
| 2021/0093918 A1 * | 4/2021 | Dervisoglu | ........... | H04W 4/021 |
| 2021/0272674 A1 * | 9/2021 | Martin | ............... | A63B 24/0062 |
| 2023/0209355 A1 * | 6/2023 | Nam | ....................... | G01S 7/006 |
| | | | | 455/456.1 |
| 2023/0390627 A1 * | 12/2023 | Bolton | .................. | G06F 3/0486 |
| 2023/0404441 A1 * | 12/2023 | Kracht | .................. | G16H 20/60 |
| 2025/0013290 A1 * | 1/2025 | Dedonato | ........... | H04W 12/065 |
| 2025/0181211 A1 * | 6/2025 | Narra | .................. | G06F 11/3476 |

OTHER PUBLICATIONS

Strava Inc., "Strava: Run, Bike, Hike", Google Play [retrieved Sep. 1, 2023]. Retrieved from the Internet <https://play.google.com/store/apps/details?id=com.strava>, 4 pages.

* cited by examiner

*Primary Examiner* — Oleg Survillo

(74) *Attorney, Agent, or Firm* — FIG. 1 Patents

(57) ABSTRACT

Techniques for activity tracking for multiple users on a device are described. For instance, the described techniques can be implemented to detect that a first user is in possession of a client device and to track physical activity of the first user as part of an activity log of the first user. The techniques can detect, via sensor data, that possession of the client device switches from the first user to a second user, and track physical activity of the second user as part of an activity log of the second user. In implementations the techniques can track physical activity of multiple users via a single device.

20 Claims, 7 Drawing Sheets

200

500

---

502
Detect that a first user is in possession of the client device and track physical activity of the first user as part of an activity log of the first user

---

504
Detect, via sensor data, that possession of the client device switches from the first user to a second user

---

506
Track physical activity of the second user as part of an activity log of the second user

---

600

602
Detect, via sensor data, that at least one of a first user or a second user is in possession of the client device 604
Track, via the client device, physical activity of the first user as part of an activity log of the first user and track physical activity of the second user as part of an activity log of the second user Device  700

Memory Device(s)
712

Device
Data
704

Device
Applications
714

Operating
System
716

Processor
System
708

Processing
&   Control
710

Power
Sources
728

Camera
722

Communication
Transceiver(s)
702

Data Input
Port(s)
706

Media Data
Port
736

Motion
Sensors
724

Device State
Module
718

Device Activity
Module
720

Audio / Video
Processing
730

Wireless Module
726

Audio
System
732

Display
System
734

ACTIVITY TRACKING FOR MULTIPLE USERS ON A DEVICE

BACKGROUND

Today's person is afforded a tremendous selection of devices that are capable of performing a multitude of tasks. Further, persons may share devices such as in household scenarios where family members may share a single device at different times for various purposes.

BRIEF DESCRIPTION OF THE DRAWINGS

Aspects of activity tracking for multiple users on a device are described with reference to the following Figures. The same numbers may be used throughout to reference similar features and components that are shown in the Figures. Further, identical numbers followed by different letters reference different instances of features and components described herein.

DETAILED DESCRIPTION

Techniques for activity tracking for multiple users on a device are described. For instance, the described techniques can be implemented to enable a mobile device to track physical activity of multiple individual users and to log (e.g., attribute) the physical activity to each individual user.

For instance, consider an environment of a household in which two spouses reside. The spouses may occasionally engage in mutual activities such as walks, hiking, bicycle riding, etc. Further, a first spouse may be a primary user (e.g., a primary registered user) of a mobile device (e.g., a mobile phone) that tracks physical activity of the primary user. A second spouse may be registered as a trusted secondary user of the mobile device.

Consider further that the spouses embark on a walk together and an activity application (e.g., a fitness tracking application) on the mobile device tracks physical activity associated with the walk as part of an activity log of the primary user, e.g., the first spouse. During the walk the secondary user (e.g., the second spouse) takes possession of the mobile device, such as to make a phone call. Accordingly, the mobile device can detect a change in physical possession of the mobile device, such as based on detecting a change in biometric attributes from the primary user to the secondary user. Thus, the activity application can detect that the secondary user is now in possession of the mobile device and can log physical activity detected via the mobile device to an activity log for the secondary user. In implementations an activity log for the primary user can continue to be updated while the secondary user is in possession of the mobile device, such as based on detecting the primary user in physical proximity to the mobile device while the secondary user is in physical proximity to the mobile device.

Thus, techniques described herein enable efficient and accurate tracking of physical activities via a single device for multiple different users.

While features and concepts of activity tracking for multiple users on a device can be implemented in any number of environments and/or configurations, aspects the described techniques are described in the context of the following example systems, devices, and methods. Further, the systems, devices, and methods described herein are interchangeable in various ways to provide for a wide variety of implementations and operational scenarios.

Figure 1:
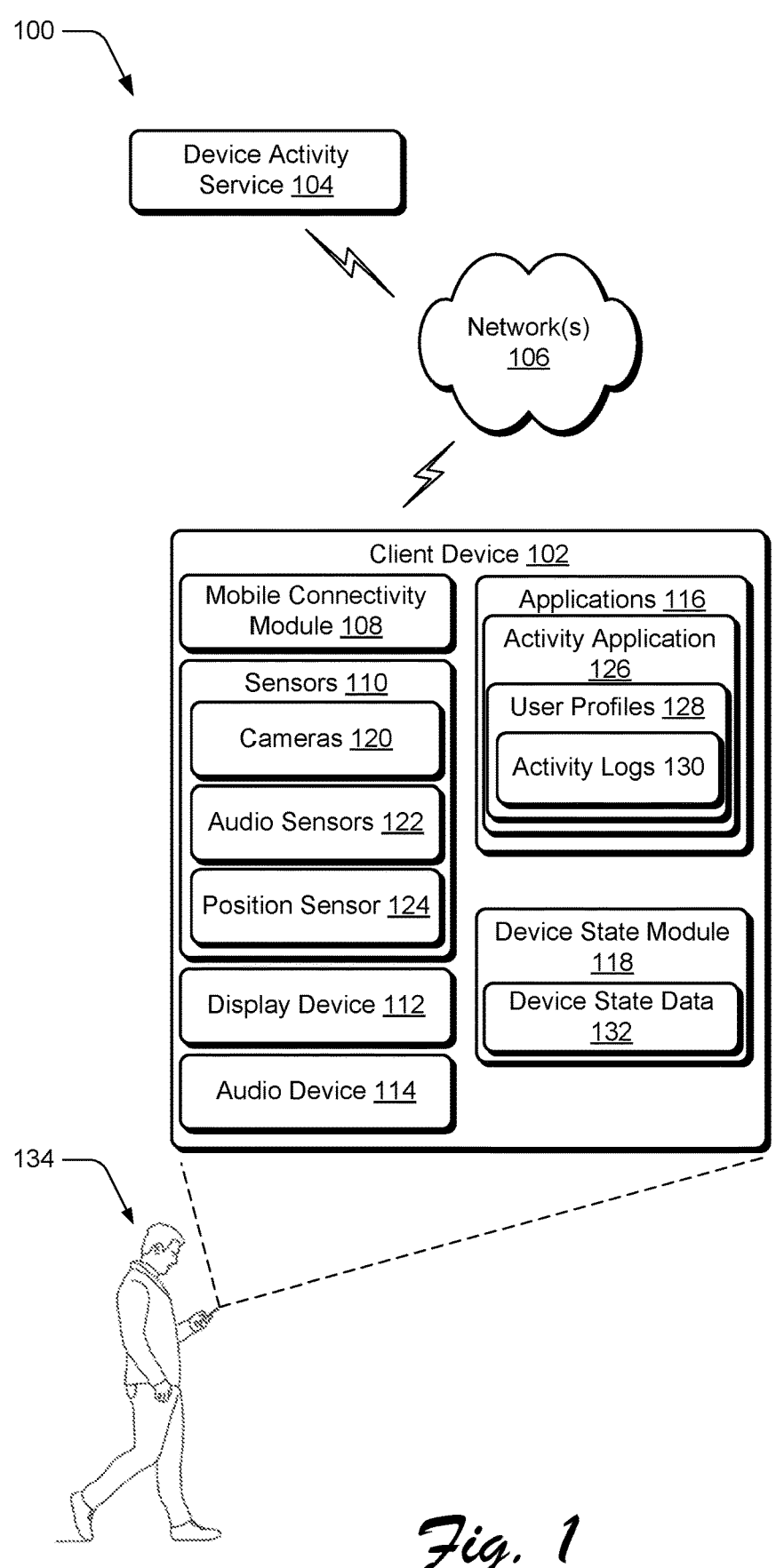
FIG. 1 illustrates an example environment 100 in which aspects of activity tracking for multiple users on a device can be implemented.

FIG. 1 illustrates an example environment 100 in which aspects of activity tracking for multiple users on a device can be implemented. The environment 100 includes a client device 102 and a device activity service 104 that are interconnectable via network(s) 106. The client device 102 can be implemented in various ways such as a mobile phone, a wearable device, a tablet device, a laptop, an extended reality (XR) device, and so forth. Example attributes and implementations of the client device 102 are discussed below with reference to the device 700 of FIG. 7.

The client device 102 includes various functionality that enables the client device 102 to perform different aspects of activity tracking for multiple users on a device discussed herein, including a mobile connectivity module 108, sensors 110, display device 112, audio device 114, applications 116, and a device state module 118. The mobile connectivity module 108 represents functionality (e.g., logic and hardware) for enabling the client device 102 to interconnect with other devices and/or networks, such as the network 106. The mobile connectivity module 108, for instance, enables wireless and/or wired connectivity of the client device 102.

The sensors 110 are representative of functionality to detect various physical and/or logical phenomena in relation to the client device 102, such as motion, light, image detection and recognition, time and date, position, location, touch detection, sound, temperature, and so forth. Examples of the sensors 110 include hardware and/or logical sensors such as an accelerometer, a gyroscope, a camera, a microphone, a clock, biometric sensors, touch input sensors, position sensors, environmental sensors (e.g., for temperature, pressure, humidity, and so on), geographical location information sensors (e.g., Global Positioning System (GPS) functionality), and so forth. In this particular example the sensors 110 include cameras 120, audio sensors 122, and a position sensor 124. The sensors 110, however, can include a variety of other sensor types in accordance with the implementations discussed herein.

The display device 112 represents functionality for outputting visual content via the client device 102 and the audio device 114 represents functionality for outputting audio content for the client device 102. The applications 116 represent functionality for performing different computing tasks via the client device 102, such as health tracking (e.g., fitness activity tracking), gaming, media consumption (e.g., content streaming), productivity tasks (e.g., email, calendar management, word processing, content generation, data analysis, etc.), content generation, web browsing, communication with other devices, and so forth.

The applications 116 include an activity application 126 which represents functionality for performing various aspects of activity tracking for multiple users on a device described herein. The activity application 126, for example, tracks user activity for different users, such as exercise activity, walking (e.g., "steps"), standing time vs. sitting time, etc. The activity application 126 includes user profiles 128 that are associated with instances of user identities and enable user attributes and user activity to be tracked for individual users. For instance, the user profiles 128 include activity logs 130 that track user activity for individual users, such as exercise activity, movement activity, rest durations (e.g., amount of sleep), etc.

The device state module 118 represents functionality for performing various aspects of activity tracking for multiple users on a device described herein. For instance, the device state module 118 can utilize sensor data from the sensors 110 to determine and monitor different device state data 132 for the client device 102. Examples of the device state data 132 for the client device 102 include device position (e.g., device location), persons interacting with and/or in possession of the client device 102, device motion, date, time of day, power states, etc. In implementations the activity application 126 can utilize device state data 132 to track user activity for different user profiles 128, e.g., to generate and update activity logs 130 for different user profiles 128. In this particular example the client device 102 is registered to a user 134.

Figure 2:
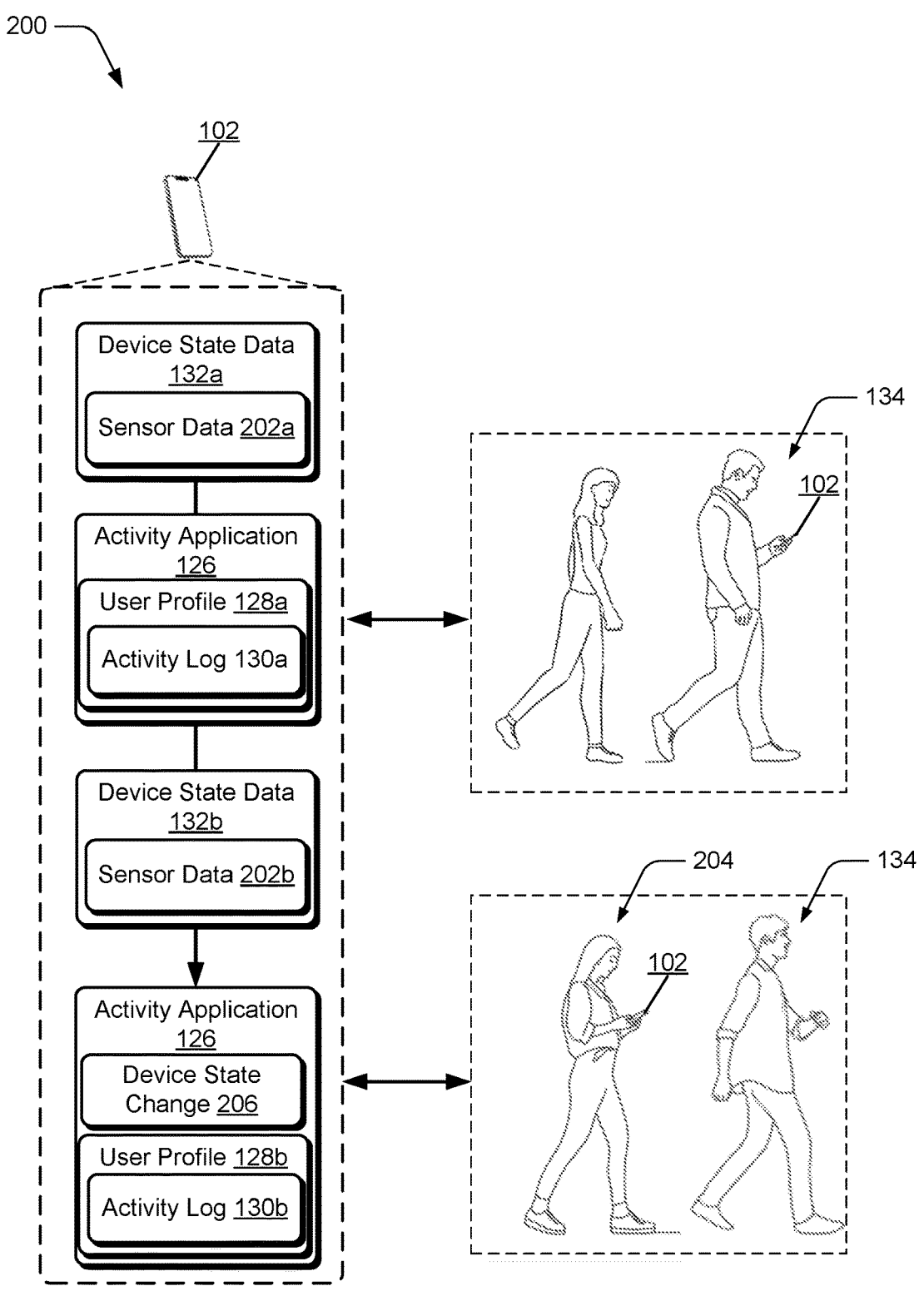
FIG. 2 illustrates an example scenario 200 for activity tracking for multiple users on a device in accordance with one or more implementations.

FIG. 2 illustrates an example scenario 200 for activity tracking for multiple users on a device in accordance with one or more implementations. In the scenario 200 device state data 132a indicates that the user 134 is in possession of the client device 102. The device state data 132a, for instance, is based at least in part on sensor data 202a received from the sensors 110. The sensor data 202a can include various types of information indicating that the user 134 is in possession of the client device 102 such as biometric sensor data for the user 134 captured by one or more of the sensors 110.

Further, the device state data 132a indicates activity information for the user 134, such as motion data (e.g., rate of movement, number of steps, etc.), duration of motion, position, biological measurements (e.g., heart rate, blood oxygen level, etc.), and so forth. Accordingly, based at least in part on the device state data 132a the activity application 126 updates an activity log 130a of a user profile 128a for the user 134. The activity log 130a, for instance, tracks physical activity of the user 134.

Further to the scenario 200 device state data 132b is generated based at least in part on sensor data 202b and the device state data 132b indicates that a user 204 is in possession of the client device 102. For example, the device state data 132b indicates a change in possession of the client device 102 from the user 134 to the user 204. "Possession" of the client device 102, for instance, represents physical custody of the client device 102, e.g., a user that is detected as physically holding the client device 102. The sensor data 202b can include various types of information indicating that the user 204 is in possession of the client device 102 such as biometric sensor data for the user 204 captured by one or more of the sensors 110. In an example implementation the users 134, 204 are engaged in a joint user activity (e.g., a walk) and the user 134 transfers possession of the client device 102 to the user 204.

Accordingly, based at least in part on the device state data 132b indicating that the user 204 is in possession of the client device 102, the activity application 126 detects a device state change 206 and updates an activity log 130b for a user profile 128b for the user 204. The activity log 130b, for instance, tracks physical activity of the user 204. Thus, implementations enable user activity for different users to be tracked, such as based on identities of users detected in possession of the client device 102.

In implementations activity logs 130 for multiple different user profiles 128 can be tracked and updated concurrently, e.g., simultaneously. For instance, in the scenario 200 sensor data from the sensors 110 can be utilized by the device state module 118 to indicate that both of the users 134, 204 are engaging in activity such as walking in proximity to each other. For example, while the user 204 is in physical possession of the client device 102 the device state module 118 can detect proximity of the user 134, such as based on image recognition, voice recognition, etc. Accordingly, the activity application 126 can concurrently update activity logs 130 for both of the users 134, 204.

Figure 3:
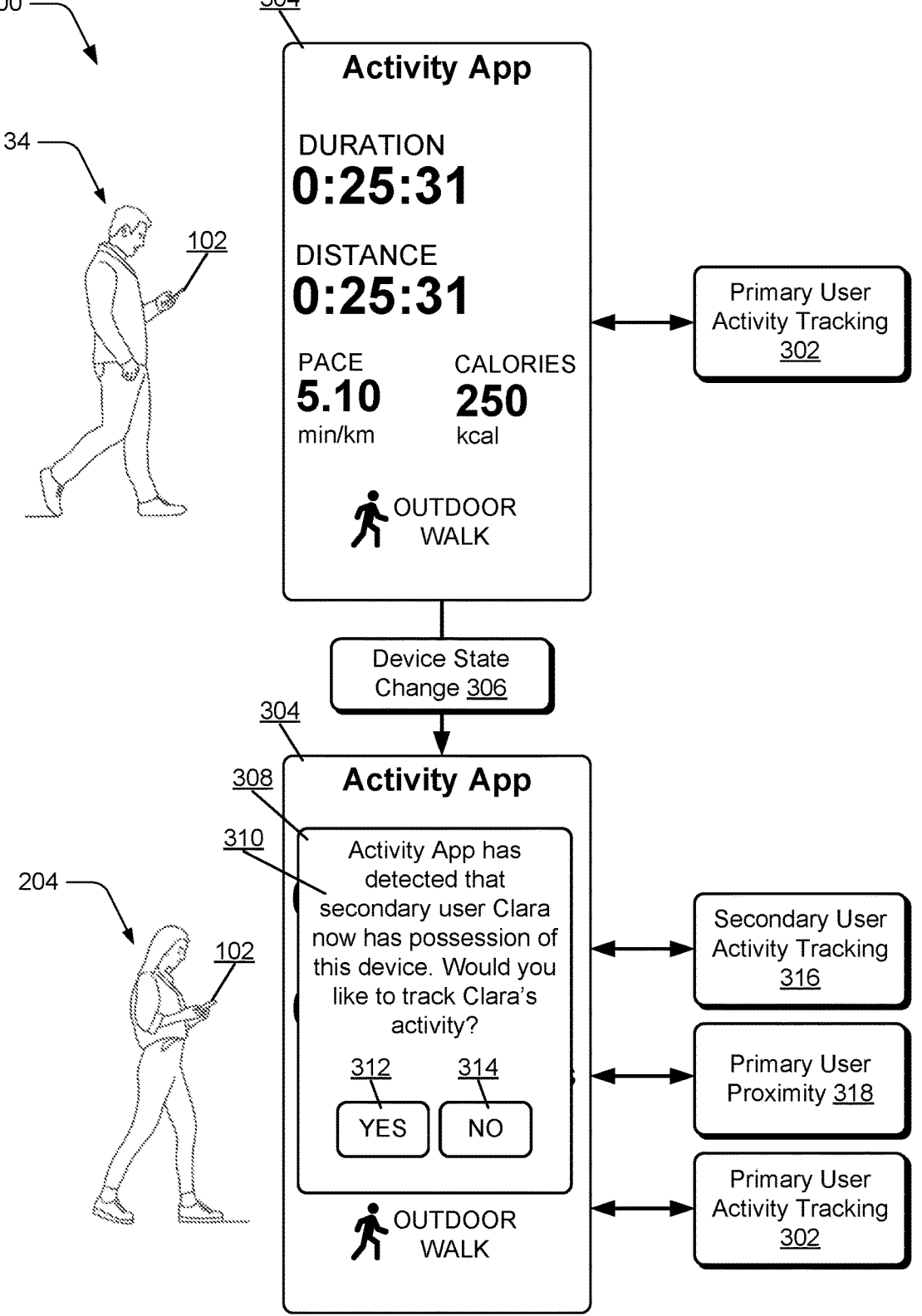
FIG. 3 illustrates an example scenario 300 for activity tracking for multiple users on a device in accordance with one or more implementations.

FIG. 3 illustrates an example scenario 300 for activity tracking for multiple users on a device in accordance with one or more implementations. In the scenario 300 the activity application 126 performs primary user activity tracking 302 for the user 134, e.g., a primary user of the client device 102. As part of the primary user activity tracking 302, the activity application 126 outputs an activity graphical user interface (GUI) 304 that includes various information about the primary user activity tracking 302, such as statistics for physical activity of the user 134 tracked as part of the primary user activity tracking 302.

Further to the scenario 300 the activity application 126 detects a device state change 306 indicating that possession of the client device 102 changes from the user 134 to the user 204. For instance, biometric sensor data captured by the sensors 110 identifies that the user 204 is in possession of the client device 102. Accordingly, the activity application 126 presents a possession change GUI 308 that includes an indication that a change in user possession of the client device 102 is detected from the primary user 134 to the secondary user 204. Further, the possession change GUI 308 includes a query 310 whether to track physical activity of the user 204, an accept control 312, and a decline control 314. For instance, the accept control 312 is selectable to cause the activity application 126 to begin tracking physical activity of the user 204 and the decline control 314 is selectable to prevent the activity application 126 from tracking physical activity of the user 204.

In the scenario 300 the accept control 312 is selected (e.g., by the user 204) and thus the activity application 126 initiates secondary user activity tracking 316. The secondary user activity tracking 316, for instance, updates an activity log 130 for the user 204 based on sensor data collected at the client device 102 by the sensors 110, such as motion data, biometric data, etc.

In at least some implementations, in conjunction with initiating the secondary user activity tracking 316, the activity application 126 detects primary user proximity 318 indicating that the user 134 is within a threshold proximity to the client device 102. The threshold proximity can be defined in various ways, such as n feet, m meters, etc. Accordingly, in response to the primary user proximity 318, the activity application 126 can continue to perform primary user activity tracking 302, such as concurrently with the secondary user activity tracking 316. Thus, physical activity for multiple users can be tracked concurrently and/or simultaneously based on motion of the client device 102 and as part of a single physical activity tracking session. Further, the activity GUI 304 can be updated to simultaneously output a representation of the primary user activity tracking 302 and a representation of the secondary user activity tracking 316.

Alternatively or additionally, the activity application 126 can switch from the primary user activity tracking 302 to the secondary user activity tracking 316. For instance, in response to the device state change 306, the activity application can stop the primary user activity tracking 302 and start the secondary user activity tracking 316. Thus, in implementations the secondary user activity tracking 316 can be performed serially to the primary user activity tracking 302.

Figure 4:
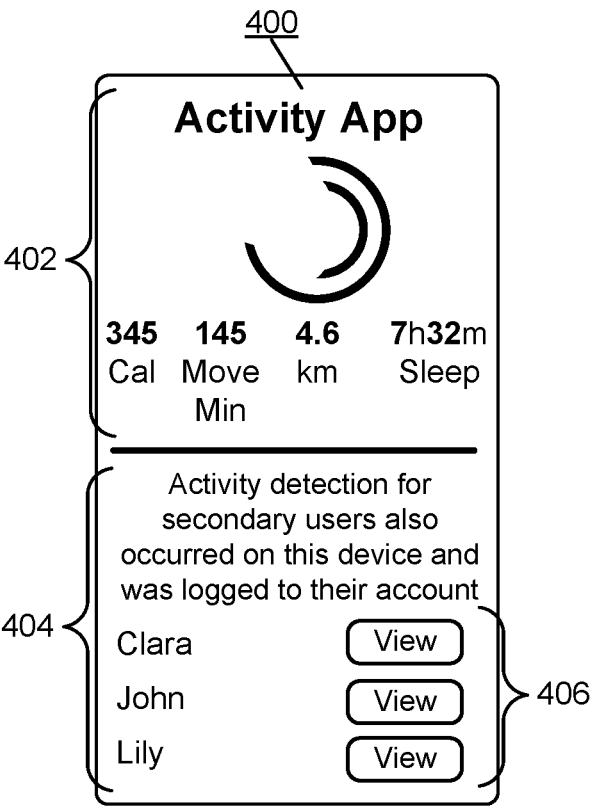
FIG. 4 illustrates an example activity summary GUI 400 in accordance with one or more implementations.

FIG. 4 illustrates an example activity summary GUI 400 in accordance with one or more implementations. The activity summary GUI 400 includes a primary user region 402 and a secondary user region 404. The primary user region 402 includes physical activity information for a primary user of the client device 102, e.g., data from an activity log 130 for the user 134. The secondary user region 404 identifies different secondary users for which physical activity has been logged by the activity application 126 via the client device 102, e.g., including the user 204. The secondary user region 404 includes view controls 406 for each secondary user and each view control 406 is selectable to view an activity log 130 for a respective secondary user.

Figure 5:
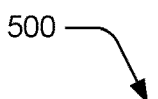
FIG. 5 illustrates a flow chart depicting an example method 500 for activity tracking for multiple users on a device in accordance with one or more implementations.

FIG. 5 illustrates a flow chart depicting an example method 500 for activity tracking for multiple users on a device in accordance with one or more implementations. At 502 it is detected that a first user is in possession of the client device and physical activity of the first user is tracked as part of an activity log of the first user. The activity application 126, for instance, determines that a primary user of the client device 102 is in possession of the client device 102 and tracks physical activity of the client device 102.

At 504 it is detected, via sensor data, that possession of the client device switches from the first user to a second user. The device state module 118, for example, generates device state data 132 using sensor data from the sensors 110, and the device state data 132 indicates that physical possession of the client device 102 switches from a primary user of the client device 102 to a secondary user of the client device 102. Various types of sensor data can be used to detect a change in device possession, such as grip detection (e.g., fingerprint detection, device contact detection), voice detection, facial recognition, etc.

At 506 physical activity of the second user is tracked as part of an activity log of the second user. The activity application 126, for example, attributes physical activity detected via the client device 102 to a secondary user of the client device 102. As discussed throughout, physical activity detected via the client device 102 can be attributed by the activity application 126 to multiple users serially, concurrently, and/or simultaneously.

Figure 6:
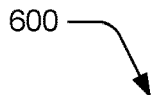
FIG. 6 illustrates a flow chart depicting an example method 600 for activity tracking for multiple users on a device in accordance with one or more implementations.

FIG. 6 illustrates a flow chart depicting an example method 600 for activity tracking for multiple users on a device in accordance with one or more implementations. At 602 it is detected, via sensor data, that at least one of a first user or a second user is in possession of the client device. The device state module 118, for instance, detects that one of a primary user or a secondary user is in possession of the client device 102. At 604 it is tracked, via the client device, physical activity of the first user as part of an activity log of the first user and track physical activity of the second user as part of an activity log of the second user. For instance, the activity application 126 tracks physical activity of the first user (e.g., a primary user) and the second user (e.g., a trusted secondary user) serially, concurrently, and/or simultaneously. Thus, in implementations multiple different activity logs 130 for multiple different users can be generated and/or updated concurrently based on physical activity detected via the client device 102.

The example methods described above may be performed in various ways, such as for implementing different aspects of the systems and scenarios described herein. Generally, any services, components, modules, methods, and/or operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like. Alternatively or in addition, any of the functionality described herein can be performed, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like. The order in which the methods are described is not intended to be construed as a limitation, and any number or combination of the described method operations can be performed in any order to perform a method, or an alternate method.

Figure 7:
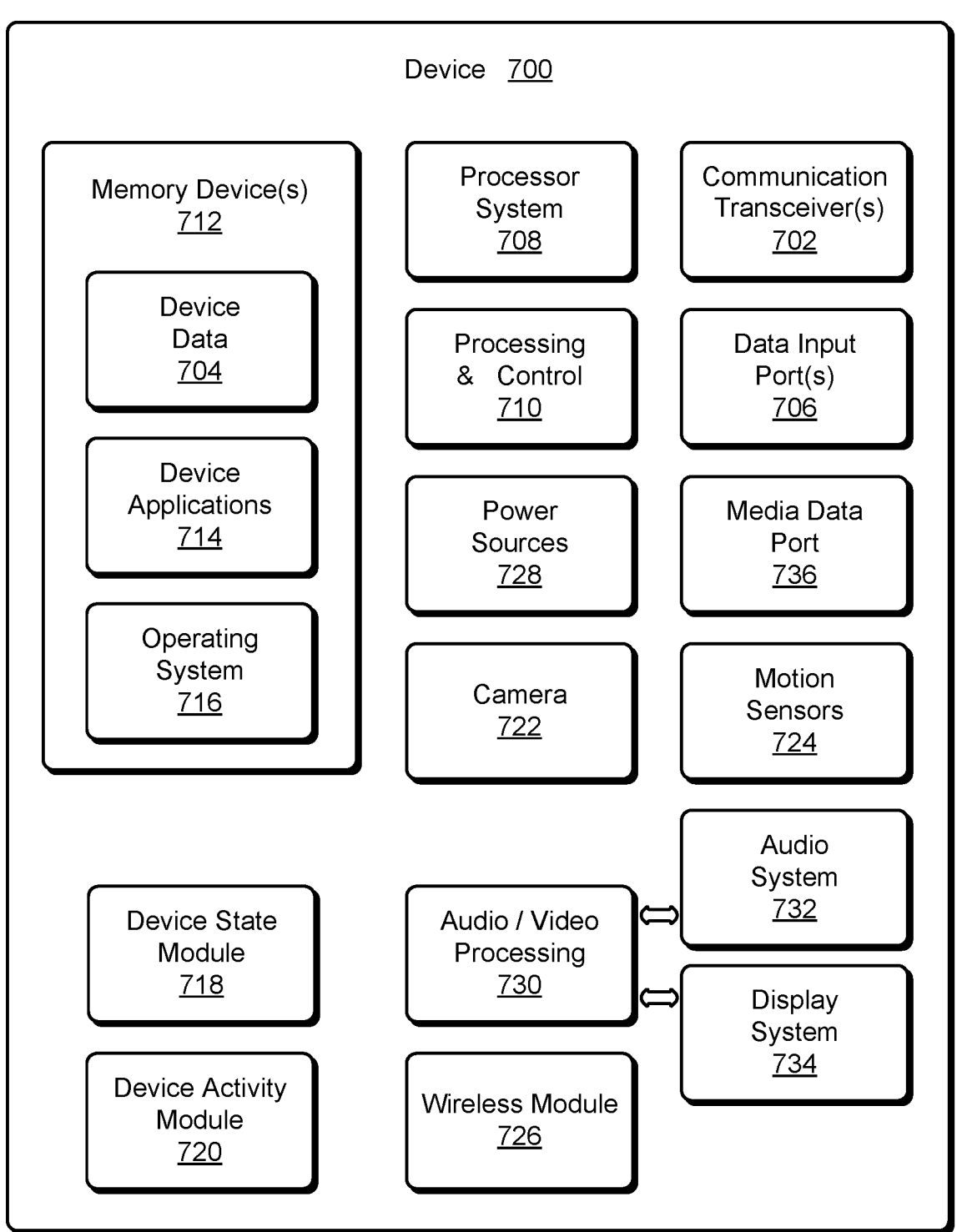
FIG. 7 illustrates various components of an example device 700 in which aspects of activity tracking for multiple users on a device can be implemented.

FIG. 7 illustrates various components of an example device 700 in which aspects of activity tracking for multiple users on a device can be implemented. The example device 700 can be implemented as any of the devices described with reference to the previous FIGS. 1-6, such as any type of client device, mobile phone, mobile device, wearable device, tablet, computing, communication, entertainment, gaming, media playback, and/or other type of electronic device. For example, the client device 102 as shown and described with reference to FIGS. 1-6 may be implemented as the example device 700.

The device 700 includes communication transceivers 702 that enable wired and/or wireless communication of device data 704 with other devices. The device data 704 can include any of device identifying data, device location data, wireless connectivity data, and wireless protocol data. Additionally, the device data 704 can include any type of audio, video, and/or image data. Example communication transceivers 702 include wireless personal area network (WPAN) radios compliant with various IEEE 802.15 (Bluetooth™) standards, wireless local area network (WLAN) radios compliant with any of the various IEEE 802.7 (Wi-Fi™) standards, wireless wide area network (WWAN) radios for cellular phone communication, wireless metropolitan area network (WMAN) radios compliant with various IEEE 802.16 (WiMAX™) standards, and wired local area network (LAN) Ethernet transceivers for network data communication.

The device 700 may also include one or more data input ports 706 via which any type of data, media content, and/or inputs can be received, such as user-selectable inputs to the device, messages, music, television content, recorded content, and any other type of audio, video, and/or image data received from any content and/or data source. The data input ports may include USB ports, coaxial cable ports, and other serial or parallel connectors (including internal connectors) for flash memory, DVDs, CDs, and the like. These data input ports may be used to couple the device to any type of components, peripherals, or accessories such as microphones and/or cameras.

The device 700 includes a processing system 708 of one or more processors (e.g., any of microprocessors, controllers, and the like) and/or a processor and memory system implemented as a system-on-chip (SoC) that processes computer-executable instructions. The processor system may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware. Alternatively or in addition, the device can be implemented with any one or combination of software, hardware, firmware, or fixed logic circuitry that is implemented in connection with processing and control circuits, which are generally identified at 710. The device 700 may further include any type of a system bus or other data and command transfer system that couples the various components within the device. A system bus can include any one or combination of different bus structures and architectures, as well as control and data lines.

The device 700 also includes computer-readable storage memory 712 (e.g., memory devices) that enable data storage, such as data storage devices that can be accessed by a computing device, and that provide persistent storage of data and executable instructions (e.g., software applications, programs, functions, and the like). Examples of the computer-readable storage memory 712 include volatile memory and non-volatile memory, fixed and removable media devices, and any suitable memory device or electronic data storage that maintains data for computing device access. The computer-readable storage memory can include various implementations of random access memory (RAM), read-only memory (ROM), flash memory, and other types of storage media in various memory device configurations. The device 700 may also include a mass storage media device.

The computer-readable storage memory 712 provides data storage mechanisms to store the device data 704, other types of information and/or data, and various device applications 714 (e.g., software applications). For example, an operating system 716 can be maintained as software instructions with a memory device and executed by the processing system 708. The device applications may also include a device manager, such as any form of a control application, software application, signal-processing and control module, code that is native to a particular device, a hardware abstraction layer for a particular device, and so on. Computer-readable storage memory 712 represents media and/or devices that enable persistent and/or non-transitory storage of information in contrast to mere signal transmission, carrier waves, or signals per se. Computer-readable storage memory 712 do not include signals per se or transitory signals.

In this example, the device 700 includes a device state module 718 and a device activity module 720 that can implement aspects of activity tracking for multiple users on a device and may be implemented with hardware components and/or in software as one of the device applications 714. For example, the device state module 718 can be implemented as the device state module 118 and the device activity module 720 can be implemented as the activity application 126. In implementations, the device state module 718 and/or the device activity module 720 may include independent processing, memory, and logic components as a computing and/or electronic device integrated with the device 700.

In this example, the example device 700 also includes a camera 722 and motion sensors 724, such as may be implemented in an inertial measurement unit (IMU). The motion sensors 724 can be implemented with various sensors, such as a gyroscope, an accelerometer, and/or other types of motion sensors to sense motion of the device. The various motion sensors 724 may also be implemented as components of an inertial measurement unit in the device.

The device 700 also includes a wireless module 726, which is representative of functionality to perform various wireless communication tasks. For instance, for the client device 102, the wireless module 726 can be leveraged to scan for and detect wireless networks, as well as negotiate wireless connectivity to wireless networks for the client device 102. The device 700 can also include one or more power sources 728, such as when the device is implemented as a mobile device. The power sources 728 may include a charging and/or power system, and can be implemented as a flexible strip battery, a rechargeable battery, a charged super-capacitor, and/or any other type of active or passive power source.

The device 700 also includes an audio and/or video processing system 730 that generates audio data for an audio system 732 and/or generates display data for a display system 734. The audio system and/or the display system may include any devices that process, display, and/or otherwise render audio, video, display, and/or image data. Display data and audio signals can be communicated to an audio component and/or to a display component via an RF (radio frequency) link, S-video link, HDMI (high-definition multimedia interface), composite video link, component video link, DVI (digital video interface), analog audio connection, or other similar communication link, such as media data port 736. In implementations, the audio system and/or the display system are integrated components of the example device. Alternatively, the audio system and/or the display system are external, peripheral components to the example device.

Although implementations of activity tracking for multiple users on a device have been described in language specific to features and/or methods, the subject of the appended claims is not necessarily limited to the specific features or methods described. Rather, the features and methods are disclosed as example implementations, and other equivalent features and methods are intended to be within the scope of the appended claims. Further, various different examples are described and it is to be appreciated that each described example can be implemented independently or in connection with one or more other described examples. Additional aspects of the techniques, features, and/or methods discussed herein relate to one or more of the following:

In addition to the previously described methods, any one or more of the following:

In some aspects, the techniques described herein relate to a client device including: one or more modules implementable at least in part in hardware of the client device to: detect that a first user is in possession of the client device and track physical activity of the first user as part of an activity log of the first user; detect, via sensor data, that possession of the client device switches from the first user to a second user; and track physical activity of the second user as part of an activity log of the second user.

In some aspects, the techniques described herein relate to a client device, wherein the one or more modules are implementable to detect that possession of the client device switches from the first user to the second user via one or more biometric attributes of the second user recognized in the sensor data.

In some aspects, the techniques described herein relate to a client device, wherein the one or more modules are implementable to determine that the first user is a primary user of the client device and the second user is a secondary user of the client device.

In some aspects, the techniques described herein relate to a client device, wherein the one or more modules are implementable to track physical activity of the second user as part of an activity log of the second user based at least in part on a determination that the second user is a trusted secondary user of the client device.

In some aspects, the techniques described herein relate to a client device, wherein the one or more modules are implementable to track physical activity of the first user as part of an activity log of the first user and track physical activity of the second user as part of an activity log of the second user serially as part of a single physical activity tracking session.

In some aspects, the techniques described herein relate to a client device, wherein the one or more modules are implementable to track physical activity of the first user as part of the activity log of the first user and track physical activity of the second user as part of the activity log of the second user concurrently as part of a single physical activity tracking session.

In some aspects, the techniques described herein relate to a client device, wherein the one or more modules are implementable to detect physical proximity of the first user to the client device while the second user is in possession of the client device.

In some aspects, the techniques described herein relate to a client device, wherein the one or more modules are implementable to output an activity GUI that presents a representation of physical activity of the first user and a representation of physical activity of the second user.

In some aspects, the techniques described herein relate to a client device, wherein the one or more modules are implementable to: output a query requesting permission to track physical activity of the second user; and track physical activity of the second user in response to an indication of acceptance of the query.

In some aspects, the techniques described herein relate to a client device including: one or more modules implementable at least in part in hardware of the client device to: detect, via sensor data, that at least one of a first user or a second user is in possession of the client device; and track, via the client device, physical activity of the first user as part of an activity log of the first user and track physical activity of the second user as part of an activity log of the second user.

In some aspects, the techniques described herein relate to a client device, wherein the one or more modules are implementable to concurrently track the physical activity of the first user as part of the activity log of the first user and track physical activity of the second user as part of the activity log of the second user.

In some aspects, the techniques described herein relate to a client device, wherein the one or more modules are implementable to detect that the first user is in possession of the client device and to detect that the second user is in physical proximity to the client device.

In some aspects, the techniques described herein relate to a client device, wherein the one or more modules are implementable to detect that the first user is a primary user of the client device and the second user is a trusted secondary user of the client device.

In some aspects, the techniques described herein relate to a client device, wherein the one or more modules are implementable to output an activity GUI that concurrently presents a representation of physical activity of the first user and a representation of physical activity of the second user.

In some aspects, the techniques described herein relate to a method, including: detecting that a first user is in possession of a client device and tracking physical activity of the first user as part of an activity log of the first user; detecting, via sensor data, that possession of the client device switches from the first user to a second user; and tracking physical activity of the second user as part of an activity log of the second user.

In some aspects, the techniques described herein relate to a method, wherein detecting, via the sensor data, that possession of the client device switches from the first user to a second user includes detecting that physical contact with the client device switches from the first user to the second user.

In some aspects, the techniques described herein relate to a method, wherein tracking physical activity of the second user as part of an activity log of the second user includes determining that the second user is a trusted secondary user of the client device.

In some aspects, the techniques described herein relate to a method, further including tracking physical activity of the first user as part of the activity log of the first user and tracking physical activity of the second user as part of the activity log of the second user serially as part of a single physical activity tracking session.

In some aspects, the techniques described herein relate to a method, further including tracking physical activity of the first user as part of the activity log of the first user and tracking physical activity of the second user as part of the activity log of the second user concurrently as part of a single physical activity tracking session.

In some aspects, the techniques described herein relate to a method, further including detecting physical proximity of the first user to the client device while the second user is in possession of the client device.

The invention claimed is:

1. A method, comprising:
detecting that a first user is in possession of a client device and tracking physical activity of the first user as part of a first activity log associated with the first user during a single physical activity tracking session;
detecting, via sensor data, that possession of the client device switches from the first user to a second user during the single physical activity tracking session; and
tracking physical activity of the second user as part of a second activity log associated with the second user during the single physical activity tracking session.

2. The method of claim 1, wherein detecting, via the sensor data, that possession of the client device switches from the first user to a second user comprises detecting that physical contact with the client device switches from the first user to the second user.

3. The method of claim 1, wherein tracking physical activity of the second user as part of the second activity log associated with the second user comprises determining that the second user is a trusted secondary user of the client device.

4. The method of claim 1, further comprising tracking physical activity of the first user as part of the first activity log associated with the first user and tracking physical activity of the second user as part of the second activity log associated with the second user serially as part of the single physical activity tracking session.

5. The method of claim 1, further comprising tracking physical activity of the first user as part of the first activity log associated with the first user and tracking physical activity of the second user as part of the second activity log associated with the second user concurrently as part of the single physical activity tracking session.

6. The method of claim 5, further comprising detecting physical proximity of the first user to the client device while the second user is in possession of the client device.

7. A client device comprising:

one or more modules implemented at least in part in hardware of the client device to:

detect that a first user is in possession of the client device and track physical activity of the first user as part of a first activity log associated with the first user during a single physical activity tracking session;

detect, via sensor data, that possession of the client device switches from the first user to a second user during the single physical activity tracking session; and track physical activity of the second user as part of a second activity log associated with the second user during the single physical activity tracking session.

8. The client device of claim 7, wherein the one or more modules are implemented to detect that possession of the client device switches from the first user to the second user via one or more biometric attributes of the second user recognized in the sensor data.

9. The client device of claim 7, wherein the one or more modules are implemented to determine that the first user is a primary user of the client device and the second user is a secondary user of the client device.

10. The client device of claim 7, wherein the one or more modules are implemented to track physical activity of the second user as part of the second activity log associated with the second user based at least in part on a determination that the second user is a trusted secondary user of the client device.

11. The client device of claim 7, wherein the one or more modules are implemented to track physical activity of the first user as part of the first activity log associated with the first user and track physical activity of the second user as part of the second activity log associated with the second user serially as part of the single physical activity tracking session.

12. The client device of claim 7, wherein the one or more modules are implemented to track physical activity of the first user as part of the first activity log associated with the first user and track physical activity of the second user as part of the second activity log associated with the second user concurrently as part of the single physical activity tracking session.

13. The client device of claim 12, wherein the one or more modules are implemented to detect physical proximity of the first user to the client device while the second user is in possession of the client device.

14. The client device of claim 7, wherein the one or more modules are implemented to output an activity GUI that presents a representation of physical activity of the first user and a representation of physical activity of the second user.

15. The client device of claim 7, wherein the one or more modules are implemented to:

output a query requesting permission to track physical activity of the second user; and track physical activity of the second user in response to an indication of acceptance of the query.

16. A client device comprising:

one or more modules implemented at least in part in hardware of the client device to:

detect, via sensor data, that at least one of a first user or a second user is in possession of the client device during a single physical activity tracking session;

detect, via sensor data, a switch in possession of the client device during the single physical activity tracking session; and track, via the client device, physical activity of the first user as part of a first activity log associated with the first user during the single physical activity tracking session and track physical activity of the second user as part of a second activity log associated with the second user during the single physical activity tracking session.

17. The client device of claim 16, wherein the one or more modules are implemented to concurrently track the physical activity of the first user as part of the first activity log associated with the first user and track physical activity of the second user as part of the second activity log associated with the second user.

18. The client device of claim 16, wherein the one or more modules are implemented to detect that the first user is in possession of the client device and to detect that the second user is in physical proximity to the client device.

19. The client device of claim 18, wherein the one or more modules are implemented to detect that the first user is a primary user of the client device and the second user is a trusted secondary user of the client device.

20. The client device of claim 16, wherein the one or more modules are implemented to output an activity GUI that concurrently presents a representation of physical activity of the first user and a representation of physical activity of the second user.

\* \* \* \* \*